United States Patent [19]
Metheny et al.

[11] Patent Number: 5,891,054
[45] Date of Patent: Apr. 6, 1999

[54] METHOD FOR DETERMINING FEEDING TUBE LOCATION

[75] Inventors: Norma Metheny; Lisa Reed Smith, both of St. Louis, Mo.; Barbara Stewart, Portland, Oreg.

[73] Assignee: Saint Louis University, St. Louis, Mo.

[21] Appl. No.: 928,298

[22] Filed: Sep. 12, 1997

[51] Int. Cl.$^6$ ........................................................ A61B 5/00
[52] U.S. Cl. ............................................. 600/584; 422/56
[58] Field of Search .................................... 600/573, 584; 604/318, 404; 422/56–60

[56] References Cited

U.S. PATENT DOCUMENTS

| | | | |
|---|---|---|---|
| 3,373,735 | 3/1968 | Gallagher | 128/2 |
| 4,069,017 | 1/1978 | Wu et al. | 23/230 |
| 4,275,031 | 6/1981 | Fischer et al. | 422/57 |
| 4,373,818 | 2/1983 | Yamamoro et al. | 356/408 |
| 4,381,011 | 4/1983 | Somers, III | 128/635 |
| 4,658,833 | 4/1987 | Stuart | 600/584 |
| 4,824,639 | 4/1989 | Hildenbrand et al. | 422/56 |
| 4,877,579 | 10/1989 | Yazawa et al. | 422/56 |
| 5,063,930 | 11/1991 | Nucci | 600/584 |
| 5,085,216 | 2/1992 | Henley, Jr. et al. | 128/636 |
| 5,105,812 | 4/1992 | Corman | 128/635 |
| 5,438,985 | 8/1995 | Essen-Moller | 128/633 |

OTHER PUBLICATIONS

Metheny, Reed, Berglund, Wehrle, "Visual Characteristics of Aspirates from feeding tubes as a Method for Predicting Tube Location", *Nursing Research*, vol. 43, No. 5, Sep./Oct. 1994, pp. 282–287.

Metheny, "Minimizing respiratory complications of nasoenteric tube feedings: State of the Science" *Heart & Lung*, vol. 22, No. 3, Jun. 1993, pp. 213–223.

Metheny, "Measures to Test Placement of Nasogastric and Naso–intestinal Feeding Tubes: A Review", *Nursing Research*, vol. 37, No. 6, Nov./Dec. 1988, pp. 324–329.

Metheny, Reed, Wiersema, McSweeney, Wehrle, Clark "Effectiveness of pH Measurements in Predicting Feeding Tube Placement: An Update" *Nursing Research*, vol. 42, No. 6, Nov./Dec. 1993, pp. 324–331.

Metheny, Clouse, Clark, Reed, Wehrle, Wiersma, "pH Testing of Feeding–Tube Aspirates to Determine Placement", *NCP*, vol. 9, No. 5, Oct. 1994, pp. 185–190.

*Primary Examiner*—Max Hindenburg
*Attorney, Agent, or Firm*—Howell & Haferkamp, LC

[57] ABSTRACT

A method for determining the position of an in vivo feeding tube. The method includes the step of sampling a bodily fluid from the distal end of an in vivo medical device. A concentration of one or more substances selected from a group consisting of bilirubin, pepsin, and trypsin contained within the bodily fluid is then identified. The position of the medical device is then determined using the concentration of the one or more substances in the sampled bodily fluid.

12 Claims, 1 Drawing Sheet

METHOD FOR DETERMINING FEEDING THE TUBE LOCATION

CROSS REFERENCE TO RELATED APPLICATION(S)

Not applicable.

STATEMENT REGARDING FEDERALLY SPONSORED RESEARCH OR DEVELOPMENT

The present invention was conceived and developed with support from the National Institutes of Health.

REFERENCE TO A MICROFICHE APPENDIX

Not applicable.

TECHNICAL FIELD

The present invention relates to a method and an apparatus for determining the position of a feeding tube in a patient, and particularly to a method and apparatus for determining the position of a feeding tube based upon the concentration of at least one of bilirubin, pepsin, and trypsin in bodily fluids aspirated from the patient through the feeding tube.

BACKGROUND OF THE INVENTION AND TECHNICAL PROBLEMS POSED BY THE PRIOR ART

Patients unable to ingest food can be provided with nourishment through the use of feeding tubes. Feeding tubes preferably are positioned to deliver enteral nutritional products to the patient's stomach or small bowel.

Feeding tubes are positioned in a patient using two primary methods. First, a feeding tube can be inserted through the patient's nose such that it passes through the esophagus and into the stomach or small bowel. Alternatively, feeding tubes can be placed percutaneously such that they pass through the patient's abdominal wall and directly into the patient's stomach. The feeding tube can be placed in the patient's small bowel using the percutaneous placement method by passing the feeding tube through the patient's abdominal wall, through the patient's stomach, and into the patient's small bowel. Feeding tubes also can be placed percutaneously directly into the patient's small bowel.

Regardless of the method by which the feeding tube is placed in a patient, it is necessary to confirm that the distal end of the feeding tube is positioned properly within the patient's gastrointestinal tract. Improper placement of the distal end of the feeding tube can result in negative health consequences. For example, it is possible that a nasogastric tube will inadvertently be placed in the patient's respiratory system, i.e., in the patient's tracheobronchial tree, in the patient's pleural space, or in the patient's lung. If an enteral nutritional product is delivered to a patient having such an inadvertently placed feeding tube, the enteral nutritional product will be delivered to the patient's respiratory system, thereby creating the potential for damage to the patient's respiratory system. For this reason, it is important to confirm that a feeding tube is not placed in the patient's respiratory system prior to the delivery of an enteral nutritional product through the feeding tube.

It also is possible for feeding tubes to "double back" during placement. For example, if a nasointestinal feeding tube is being placed into the small bowel, the feeding tube is fed through the patient's esophagus and stomach until it is properly positioned within the small bowel. However, due to the anatomy of the stomach and the pylorus, it is possible for the feeding tube to reverse directions in the stomach and return to the esophagus as it is fed into the patient. Thus, the distal end of the feeding tube may inadvertently be placed in the patient's esophagus rather than in the patient's small bowel. The positioning of the feeding tube in the esophagus also may have detrimental health consequences as there is an increased risk that an enteral nutritional product delivered through such a feeding tube will migrate to the patient's respiratory system, e.g., as a result of aspiration by the patient.

In some cases it is important to confirm the precise location of the feeding tube within the patient's gastrointestinal tract. For example, it may be preferable to place the feeding tube in the patient's small bowel in order to reduce the likelihood that the enteral nutritional product will be aspirated by the patient. The potential for aspiration exists when fluids move upwardly into the patient's esophagus, thereby creating an opportunity for the fluids to migrate into the patient's respiratory system. The potential for aspiration is decreased when an enteral nutritional product is delivered into the patient's small bowel. The patient's disease state may also dictate a preferred placement of the distal end of the feeding tube.

The most common methodologies for determining feeding tube placement are (a) radiography; and (b) auscultation. Radiographic techniques require that the patient be subjected to X-rays for the purpose of determining the precise location of the distal end of the feeding tube. Such techniques can be time consuming due to the fact that the patient must be moved to an X-ray laboratory in order to confirm feeding tube placement. Alternatively, a portable X-ray apparatus may need to be transported to the patient's bedside to confirm feeding tube placement. In addition, X-ray verification of feeding tube placement is a relatively costly procedure. Finally, safety concerns regarding the exposure of patient's to X-rays must be considered.

Auscultation entails the introduction of air through the feeding tube. As the air is introduced into the patient's feeding tube, a medical professional uses a stethoscope to listen for abdominal sounds produced by the air. A failure to clearly hear loud sounds may indicate that the feeding tube has been inadvertently placed in the patient's respiratory system instead of the gastrointestinal tract. However, auscultation may be inconclusive because sounds may be transmitted to the abdominal area even when the feeding tube is in the respiratory system. For example, it has been found that a minor gurgling sound may be referred to the gastrointestinal tract in some patients even though the distal end of the feeding tube is positioned within the patient's respiratory tract or in the patient's pleural space. This minor gurgling sound can be misinterpreted as an indication that the feeding tube is placed correctly in the gastrointestinal tract.

An alternative methodology for determining feeding tube location entails the placement of the proximal end of the feeding tube (the end positioned external to the patient) in a container of liquid. This methodology theorizes that a feeding tube inadvertently placed in a patient's respiratory system will produce bubbles in the liquid as the patient exhales. However, placement of the feeding tube in bronchioles may occlude the port or ports on the distal end of the feeding tube, thereby precluding the passage of air through the tube. Alternatively, the port or ports of the feeding tube may be lodged against pleural tissues, thereby precluding the passage of air through the tube.

Yet another methodology for determining feeding tube location entails the monitoring of the patient for signs of respiratory distress such as coughing, dyspnea, or cyanosis. This methodology may be inconclusive in patients having decreased levels of consciousness, diminished cough or gag reflexes, and/or temporary laryngeal incompetence. Further, the delivery of even a small amount of an enteral nutritional product into a patient's respiratory system may produce deleterious health consequences. Thus, merely waiting for the manifestations of improper feeding tube placement may not be adequate for many patients.

U.S. Pat. No. 3,373,735 to Gallagher discloses a method for determining feeding tube location using the pH of fluids aspirated through the feeding tube. However, this methodology also has drawbacks in that fluids aspirated from both the small bowel and the respiratory system are usually alkaline while gastric fluids are acidic. Thus, the pH method can be used to confirm gastric placement, but cannot be used to differentiate between placement in the respiratory system and placement in the small bowel. Further, medications can significantly increase the pH of gastric fluids, thereby rendering the pH methodology useless in certain groups of patients.

SUMMARY OF THE INVENTION

According to one aspect of the present invention, a method is provided for determining the position of a feeding tube. The method includes the steps of sampling a bodily fluid at a distal end of a feeding tube. A concentration of one or more substances from a group consisting of bilirubin, pepsin, and trypsin is identified for the sampled fluid. The selected concentration is then used to determine the position of the distal end of the feeding tube.

According to another aspect of the present invention, an apparatus for determining the position of a feeding tube is provided. The apparatus is constructed to determine the concentration of bilirubin in a fluid and to provide an indication thereof.

BRIEF DESCRIPTION OF THE DRAWINGS

In the accompanying drawings that form part of the specification, and in which like numerals are employed to designate like parts throughout the same.

DESCRIPTION OF THE PREFERRED EMBODIMENT

Figure 1:
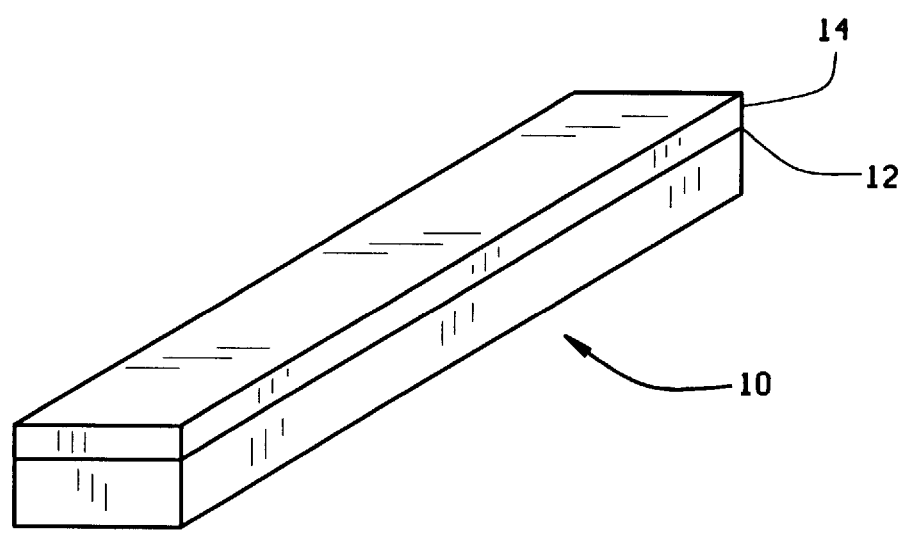
FIG. 1 is an elevational view of an apparatus constructed in accordance with the present invention.

The position of a distal end of an in vivo feeding tube is determined in accordance with the method of the present invention by sampling a quantity of fluid from the environment surrounding the distal end of the feeding tube. For the purposes of this discussion, the distal end of the feeding tube is the end positioned within the patient's body while the proximal end of the feeding tube is the end positioned externally to the patient's body. The present method can be used to determine the position of the distal end of a newly placed feeding tube, or to determine the position of the distal end of a feeding tube that has been in vivo for a period of time. The distal end of the in vivo feeding tube generally is in contact with a bodily fluid regardless of whether it is positioned within the respiratory system, the stomach, the small bowel, or some other portion of the gastrointestinal tract.

Although the apparatus and method of the present invention are described herein in the context of determining feeding tube location, it will be appreciated that the apparatus and method of the present invention can be used to determine the position of other known medical devices that are placed in the gastrointestinal tract or in the respiratory system.

Sampling can be conducted at the distal end of the feeding tube or at the proximal end of the tube. If sampling is conducted at the proximal end of the feeding tube, fluid is drawn or aspirated through the feeding tube from its distal end to its proximal end. Fluid can be drawn through the feeding tube using a variety of known techniques, including the application of a suction force or vacuum at the proximal end of the feeding tube. For example, a syringe or other vacuum-forming apparatus typically used in medical procedures can be placed in fluid communication with the lumen of the feeding tube at the proximal end thereof in order to draw fluid from the distal end of the tube outwardly to the proximal end of the tube.

An apparatus for identifying a concentration of one or more of bilirubin, pepsin, and trypsin in the aspirated fluid is generally depicted at 10 in FIG. 1. In one embodiment, the apparatus 10 for identifying further is configured to determine the pH of the aspirated fluid. The apparatus 10 for identifying can employ known laboratory testing procedures for determining bilirubin, pepsin, and/or trypsin concentrations. The apparatus may further include known laboratory testing procedures for determining pH. For example, litmus paper can be used to determine the pH of the aspirated fluid. Alternatively, the apparatus for identifying can be a diagnostic test kit or strip developed specifically for use in connection with the method of the present invention. Additional information regarding the apparatus for identifying is set forth below.

If sampling is conducted at the distal end of the feeding tube, the apparatus for identifying is preferably positioned at the distal end of the feeding tube, thereby obviating the need to aspirate fluid from the distal end to the proximal end of the feeding tube. In such an embodiment, a means for conveying to the proximal end of the feeding tube (or to another point outside of the patient's body) the bilirubin, pepsin, and/or trypsin concentrations detected by the apparatus for identifying is provided. For example, a means for conveying can be constructed to transfer an electronically encoded signal generated by the apparatus for identifying, such transfer being directed from the distal end of the feeding tube to the proximal end of the feeding tube, or to another point exterior to the patient's body. One example of such a means for conveying is an electrical signal transmitting wire extending from the distal end to the proximal end of the feeding tube. In an alternative embodiment, the means for conveying can convey the encoded signal through the use of electrical and/or magnetic signal generating and receiving devices of known construction and operation. It will be appreciated that in those embodiments in which a pH of the fluid also is determined, the means for conveying is further configured to communicate pH information from the distal end of the tube to the proximal end of the tube.

If sampling is conducted at the proximal end of the feeding tube, the apparatus for identifying can be positioned adjacent to the proximal end of the feeding tube. Alternatively, the apparatus for identifying can be separated from the feeding tube, in which case a vessel for collecting and transferring the aspirated fluids is preferably provided. For example, if a syringe is used to aspirate fluid from the distal end of the feeding tube, the aspirated fluid can be collected and stored in the syringe and subsequently transferred to the apparatus for identifying. Alternatively, a vessel of known construction can be used to collect the aspirated fluid. In a preferred embodiment, the vessel is substantially closed to the external environment, thereby minimizing the possibility of contamination and/or spillage of the aspirated fluid. The aspirated fluid is then delivered from the vessel to the apparatus for identifying.

After the aspirated fluid has been delivered to the apparatus for identifying, a concentration of one or more of pepsin, trypsin, and bilirubin in the aspirated fluid is determined. The resulting concentration or concentrations are then used to determine the position of the distal end of the feeding tube in accordance with the method of the present invention, as discussed in greater detail herein.

Bilirubin

The inventor conducted studies to determine the bilirubin content of bodily fluids from different portions of the respiratory system and gastrointestinal tract. The precise bilirubin content was measured using known spectrophotometric procedures.

The inventor's studies indicate that approximately 89% of fluids aspirated from the respiratory system have a bilirubin concentration of 0 mg/dl. Approximately 10.5% of fluids aspirated from the respiratory system have a bilirubin concentration greater than 0 mg/dl and less than 2 mg/dl. Approximate 0.5% of fluids aspirated from the respiratory system have a bilirubin concentration greater than or equal to 2 mg/dl and less than 5 mg/dl. The mean bilirubin concentration for fluids aspirated from the respiratory system was determined to be approximately 0.08 mg/dl.

The inventor's studies also indicate that approximately 47% of fluids aspirated from the stomach have a bilirubin concentration of 0 mg/dl. Approximately 40% of fluids aspirated from the stomach have a bilirubin concentration greater than 0 mg/dl and less than 2 mg/dl. Approximately 5.5% of fluids aspirated from the stomach have a bilirubin concentration greater than or equal to 2 mg/dl and less than 5 mg/dl. Approximately 5.5% of fluids aspirated from the stomach have a bilirubin concentration greater than or equal to 5 mg/dl and less than 10 mg/dl. Approximately 1% of fluids aspirated from the stomach have a bilirubin concentration greater than or equal to 10 mg/dl and less than 15 mg/dl. Approximately 1% of fluids aspirated from the stomach have a bilirubin concentration greater than or equal to 15 mg/dl. The mean bilirubin concentration for fluids aspirated from the stomach was determined to be approximately 1 mg/dl.

The inventor's studies also indicate that approximately 0% of fluids aspirated from the small bowel have a concentration of 0 mg/dl. Approximately 8.9% of fluids aspirated from the small bowel have a bilirubin concentration greater than 0 mg/dl and less than 2 mg/dl. Approximately 13.8% of fluids aspirated from the small bowel have a bilirubin concentration greater than or equal to 2 mg/dl and less than 5 mg/dl. Approximately 33.8% of fluids aspirated from the small bowel have a bilirubin concentration greater than or equal to 5 mg/dl and less than 10 mg/dl. Approximately 16.4% of fluids aspirated from the small bowel have a bilirubin concentration greater than or equal to 10 mg/dl and less than 15 mg/dl. Approximately 27.1% of fluids aspirated from the small bowel have bilirubin concentrations greater than or equal to 15 mg/dl. The mean bilirubin concentration for fluids aspirated from the small bowel was determined to be greater than about 12 mg/dl.

The mean bilirubin concentration of fluids aspirated from the respiratory system thus is less than one-tenth of the mean bilirubin concentration of fluids aspirated from the stomach and less than one-hundredth of the mean bilirubin concentration of fluids aspirated from the small bowel. From the foregoing, it is apparent that the concentration of bilirubin in aspirated fluids can be used to determine the position of the distal end of a feeding tube. Thus, the method for determining feeding tube location in accordance with the present invention entails a determination of the concentration of bilirubin at the distal end of a feeding tube. The position of the feeding tube is then determined based upon the bilirubin concentration.

It has been discovered that the combination of bilirubin concentration and pH of the aspirated fluid provides a greater degree of certainty with respect to tube position when compared to bilirubin concentration alone. A separate, detailed discussion of the pH of aspirated bodily fluids is set forth below. It is known that the pH of fluids aspirated from the stomach will be significantly lower than the pH of fluids aspirated from the respiratory system or the small bowel due to the acidity of gastric juices. Thus, pH can be used to determine whether a feeding tube is positioned within the stomach, but cannot be used to distinguish respiratory placement from small bowel placement. For example, a pH of less than 5 can be used to establish definitively that the feeding tube is not positioned in the respiratory system. Higher pH levels, e.g., 5–6.5, can be used to establish that the tube is not positioned in the respiratory system, but it will be appreciated that the higher the cut off pH level, the lower the certainty that the feeding tube is not placed in the respiratory system. Although pH can be used to exclude respiratory placement, it cannot be used readily to distinguish between respiratory and small bowel placement of a feeding tube. Thus, by using pH as an initial factor in determining feeding tube location, it is possible to determine whether the tube is positioned (a) in the stomach; or (b) in the respiratory system or in the small bowel.

If the pH indicates that the feeding tube is positioned in either the small bowel or in the respiratory system, bilirubin concentration can be used to distinguish between respiratory placement and small bowel placement. As above-discussed, it is known that the mean bilirubin concentration of fluids aspirated from the small bowel is more than one-hundred times the mean bilirubin concentration of fluids aspirated from the respiratory system. Thus, a bilirubin concentration cut off point between these respective mean bilirubin concentrations can be used to distinguish respiratory placement from small bowel placement. For example, a bilirubin concentration of 5 mg/dl can be used as the cut off point. If the aspirated fluid has a bilirubin concentration greater than or equal to 5 mg/dl, the feeding tube is most likely positioned in the small bowel. If the aspirated fluid has a bilirubin concentration less than 5 mg/dl, the feeding tube is most likely positioned in the respiratory system. It should be remembered that this differentiation between respiratory and small bowel placement using bilirubin concentration is made in conjunction with the above-discussed determination of gastric or non-gastric placement using the pH of the aspirated fluid.

Although a bilirubin concentration of 5 mg/dl is used as an example herein, it will be appreciated that lower bilirubin concentrations, e.g., 3 mg/dl or 4 mg/dl, or higher bilirubin concentrations, e.g., 6 mg/dl or 7 mg/dl, also indicate that the distal end of the feeding tube is not positioned in the patient's respiratory system. However, the lower the bilirubin concentration used as a cut off point, the greater the possibility that the feeding tube is placed in the respiratory system rather than in the gastrointestinal tract. Thus, it is preferable that the cut off point be sufficiently high to ensure that the feeding tube is not positioned within the respiratory system. The preferred cut-off bilirubin concentration is 5 mg/dl.

The combination bilirubin pH test can be summarized as follows: (a) if the pH of the fluid is less than a selected threshold level, e.g., 5, the feeding tube is positioned in the stomach; (b) if the pH of the fluid is greater than or equal to 5 and the bilirubin concentration is less than 5 mg/ml, the feeding tube is positioned in the respiratory system; (c) if the pH of the fluid is greater than or equal to 5 and the bilirubin concentration is greater than or equal to 5 mg/dl, the feeding tube is positioned in the small bowel. It is to be remembered that different threshold levels for pH and bilirubin can be used in conjunction with the method of the present invention with departing from the spirit and scope thereof.

From the foregoing it is apparent that the concentration of bilirubin in fluids aspirated from the distal end of a feeding tube can be used to determine the location of the distal end of the feeding tube. For this reason, an apparatus for identifying bilirubin concentration in aspirated fluids was developed. FIG. 1 depicts a representation of an apparatus 10 constructed in accordance with this aspect of the present invention. The apparatus 10 includes a surface 12 having thereon a reactive substrate 14 for receiving the aspirated fluid. The reactive substrate 14 can include any known reactive reagent for bilirubin. For example, Sigma Diagnostics Company of St. Louis, Mo. manufactures an appropriate reagent containing 0.4% w/w 2,4-dichloroaniline diazonium salt, 37.3% w/w buffer and 62.3% w/w nonreactive ingredients.

In one embodiment of the apparatus of the present invention, the apparatus 10 for identifying bilirubin concentration is configured such that it provides a visual indication of the bilirubin content of the aspirated fluids. For example, the apparatus can be configured to provide a different color for each of a plurality of different bilirubin concentrations. In a preferred embodiment of the present invention, the apparatus 10 is configured to provide a visual indication of bilirubin concentration by displaying a different color for each of the following ranges of bilirubin concentrations: (a) greater than or equal to 0 mg/dl and less than 2 mg/dl; (b) greater than or equal to 2 mg/dl and less than 5 mg/dl; (c) greater than or equal to 5 mg/dl and less than 10 mg/dl; and (d) greater than or equal to 10 mg/dl and less than 15 mg/dl; and (e) greater than or equal to 15 mg/dl. It will be appreciated that other embodiments of apparatus 10 utilizing different bilirubin concentration ranges are possible. For example, in connection with the above-discussed example, apparatus 10 can be configured to provide a visual indication of bilirubin concentrations (a) less than 5 mg/dl; and (b) greater than or equal to 5 mg/dl. As above-discussed, the bilirubin concentrations selected will affect the certainty with which apparatus 10 of the present invention determines feeding tube location.

Although the preferred embodiment of the apparatus of the present invention provides a visual indication of the concentration of bilirubin in the sample fluid by way of a range of colors, it will be apparent to one of ordinary skill that other indications of bilirubin concentration can be used. For example, the apparatus of the present invention can be configured to provide a numerical indication of the bilirubin concentration. This numerical indication can be read and interpreted by an individual operating the apparatus, or the numerical indication can be transferred to another apparatus, e.g., a CPU, that provides an interpretation of the numerical indication. In addition, other visual indications of bilirubin concentration can be used in lieu of the range of colors utilized by the preferred embodiment of the present invention. For example, the apparatus can be configured to provide a positive or negative reading indicating which of the above-referenced ranges of bilirubin concentrations is present in the aspirated fluid. The apparatus also can be configured to indicate whether a threshold level of bilirubin is present in the fluid. The threshold bilirubin value used preferably will be determined in accordance with the description contained in this application.

The apparatus of the present invention can further include a means for determining the pepsin and trypsin concentrations of a sample fluid. The means for determining pepsin and trypsin concentrations can be incorporated into substrate 14 or can be separate from substrate 14. The means for determining pepsin and trypsin concentrations can be included on strip 12 or can be included on a separate testing device where the separate testing device and strip 12 constitute apparatus 10. Known substrates for determining pepsin and trypsin concentrations can be used as the means for determining pepsin and trypsin concentrations. The means for determining can be configured to provide absolute values for pepsin and/or trypsin concentrations, or, in the alternative, can be configured to indicate the presence of absence of a threshold level of pepsin and/or trypsin in the sample fluid. The threshold pepsin and trypsin values used preferably will be determined in accordance with the description contained in this application.

Pepsin

The inventor conducted studies to determine the pepsin content of certain bodily fluids. The precise pepsin content of the bodily fluids was measured using known spectrophotometric procedures.

Pepsin activity typically terminates when gastric contents mix with the alkaline contents of the small bowel, with pepsin being completely destroyed at a pH greater than 8. For this reason, pepsin is expected to be found in fluids aspirated from the stomach, but is not expected to be found in fluids aspirated from the small bowel. Further, pepsin is not expected to be found in fluids aspirated from the patient's respiratory system unless the patient has aspirated gastric fluids into the respiratory system. For this reason, the presence of pepsin in fluids aspirated from a patient's lung indicates that the patient has experienced pulmonary aspiration.

The present invention includes a method for determining whether a patient has experienced pulmonary aspiration. This aspect of the method of the present invention includes the steps of sampling fluid from the patient's respiratory system and determining the concentration of pepsin in the sampled fluid. The presence of pepsin in the sample fluid will indicate that the patient has experienced pulmonary aspiration while the absence of pepsin in the sample fluid will indicate that the patient has not experienced pulmonary aspiration. In order to increase the degree of certainty, a threshold pepsin concentration, e.g., 100 $\mu$g/ml, can be used as cut-off point for indicating whether the patient has experienced pulmonary aspiration.

The inventor's studies indicate that pepsin levels in the small bowel fall between 0 $\mu$g/ml and 784.3 $\mu$g/ml with a mean concentration of 24.2 $\mu$g/ml and a median concentration of 0.0 $\mu$g/ml. The inventor's studies also indicate that pepsin levels in the stomach fall between 0 $\mu$g/ml and 1164 $\mu$g/ml with a mean concentration of 349.2 $\mu$g/ml and a median concentration of 313.2 $\mu$g/ml. Finally, the inventor's studies indicate that pepsin levels in the respiratory system fall between 0 $\mu$g/ml and 83.1 $\mu$g/ml with a mean concentration of 3.2 $\mu$g/ml and a median concentration of 0.0 $\mu$g/ml.

From the foregoing, it is apparent that the pepsin concentration of bodily fluids can be used to determine the position of the distal end of a feeding tube through which the bodily fluids are sampled. That is, a pepsin concentration other than zero indicates that the feeding tube is most likely positioned within the stomach. In order to increase the likelihood that the feeding tube is positioned in the stomach, a threshold pepsin concentration above zero, e.g., 100 µg/ml–200 µg/ml, can be used to indicate that the distal end of the feeding tube is positioned within the stomach.

In a majority of patients it will not be possible to distinguish between respiratory and small bowel tube placement using pepsin concentration due to the fact that the median concentration of pepsin in both the respiratory system and the small bowel is zero.

Trypsin

The inventor conducted studies to determine the trypsin content of certain bodily fluids. The precise trypsin content was measured using known spectrophotometric procedures.

Pancreatic fluid rich in trypsin empties into the duodenum approximately 10 cm below the pylorus. Thus, the presence of trypsin is a likely indicator that a feeding tube is positioned in the small bowel. However, it is conceivable that trypsin will be found in the stomach following duodenogastric reflux. It is highly unlikely that trypsin will be found in fluids in the respiratory system.

The inventor's studies indicate that trypsin levels in the small bowel fall between 0 µg/ml and 853.0 µg/ml with a mean concentration of 143.0 µg/ml and a median concentration of 104.3 µg/ml. The inventor's studies also indicate that trypsin levels in the stomach fall between 0 µg/ml and 320.0 µg/ml with a mean concentration of 19.3 µg/ml and a median concentration of 0 µg/ml. Finally, the inventor's studies indicate that trypsin levels in the respiratory system fall between 0 µg/ml and 26.0 µg/ml with a mean concentration of 1.4 µg/ml and a median concentration of 0.0 µg/ml.

From the foregoing, it is apparent that the trypsin concentration of bodily fluids can be used to determine the position of the distal end of a feeding tube through which the bodily fluids are sampled. For example, the presence of trypsin in a bodily fluid aspirated through a feeding tube indicates that the distal end of the feeding tube is most likely placed in the patient's small bowel. In order to increase the likelihood that the feeding tube is positioned in the small bowel, a threshold trypsin concentration above zero, e.g., 30 µg/ml–50 µg/ml, can be used to indicate that the distal end of the feeding tube is positioned within the small bowel.

In a majority of patients it will not be possible to distinguish between respiratory and stomach tube placement using trypsin concentration due to the fact that the median concentration of trypsin in both the respiratory system and the stomach is zero.

pH

The pH of fluids aspirated from the stomach is expected to be much lower than the pH of fluids aspirated from the respiratory system or from the small bowel. The inventor's studies indicate that pH levels in the small bowel fall between of 1.7–8.8 with a mean pH of 7.4 and a median pH of 7.6. The inventor's studies also indicate that pH levels in the stomach fall between 0.9–9.0 with a mean pH of 4.0 and a median pH of 3.7. Finally, the inventor's studies indicate that pH levels in the respiratory system fall between 5.5 and 8.9 with a mean pH of 7.9 and a median pH of 7.9. Thus, a bodily fluid having an acidic pH was most likely aspirated from the stomach. In order to increase the likelihood that distal end of the feeding is actually positioned in the stomach, a threshold pH of less than 7, e.g., 5, is preferably used. It will be appreciated that the lower the pH threshold, the more likely it will be that the feeding tube is actually positioned in the stomach.

In a majority of patients it will not be possible to distinguish between respiratory and small bowel tube placement using pH.

Combinations

Although concentrations of bilirubin, pepsin, and trypsin in aspirated fluids can be used individually to determine the position of the distal end of a feeding tube, it has been found that combinations of these tests with each other or with pH may provide an enhanced method for determining feeding tube placement. A method entailing the use of both bilirubin concentration and pH was discussed above. Additional combination methodologies will now be discussed.

As above-indicated, pH alone cannot distinguish between respiratory and small bowel placement of the feeding tube because bodily fluids aspirated from each location will have comparable pH levels. On the other hand, pH can be used to establish that the feeding tube is most likely positioned in the stomach, i.e., when the pH is acidic, e.g., $\leq 5$. As above-discussed, bilirubin concentration can be used to determine whether the feeding tube is most likely positioned in the respiratory system or in the small bowel when the pH of the aspirated fluid is greater than 5 (or some other acidic threshold level).

The trypsin concentration of the aspirated bodily fluid also can be used to distinguish between respiratory and small bowel tube placement. For example, if the pH of the aspirated fluid is greater than a threshold value of 5 (or some other acidic threshold level) and the trypsin concentration of the aspirated fluid is less than or equal to a threshold trypsin concentration, e.g., 30 µg/ml, the feeding tube is most likely positioned within the respiratory system. If the aspirated fluid has a pH greater than a threshold level, e.g., 5, and a trypsin concentration greater than a threshold level, 30 µg/ml, the feeding tube is most likely positioned in the small bowel. It will be appreciated that thresholds other than 30 µg/ml and pH=5 can be used without departing from the intended spirit and scope of the present invention.

As set forth herein, trypsin and bilirubin concentrations can be used to determine whether the feeding tube is positioned within the small bowel. Thus, a combination test employing both trypsin and bilirubin concentrations will provide confirmation as to whether or not the feeding tube is positioned within the small bowel. Such a combination test will preferably employ threshold concentrations such as those discussed herein. It will be appreciated that a combination test employing trypsin and bilirubin concentrations will not distinguish between respiratory and gastric feeding tube placement.

The concentration of pepsin in the aspirated bodily fluid can be used to determine if the distal end of the feeding tube is positioned in the stomach. For example, a pepsin concentration of at least 100 µg/ml (or some other threshold level) will indicate that the distal end of the feeding tube is positioned in the stomach while a pepsin concentration of less than 100 µg/ml (or some other threshold level) will indicate that the distal end of the feeding tube is not positioned in the stomach. Pepsin concentration cannot be used readily to distinguish between respiratory and small bowel tube placement. However, the bilirubin concentration of the aspirated fluid can be used to distinguish between respiratory and small bowel placement after the pepsin concentration has been used to exclude the possibility of stomach placement. For example, a threshold bilirubin concentration of 5 mg/dl can be used to provide the requisite distinction between respiratory and small bowel placement after gastric placement has been excluded based upon the pepsin concentration. That is, a bilirubin concentration of less than 5 mg/dl (or an alternative threshold level) will indicate that the feeding tube is positioned in the respiratory system while a bilirubin concentration greater than or equal to 5 mg/dl (or an alternative threshold level) will indicate that the feeding tube is positioned in the small bowel. Thus, a combination test employing pepsin and bilirubin concentrations, or threshold levels of pepsin and bilirubin, can be used to determine whether a feeding tube is positioned in the respiratory system, the stomach, or the small bowel.

In lieu of bilirubin in the previous paragraph, the trypsin concentration of the aspirated fluid can be used to determine whether the distal end of the feeding tube is positioned within the small bowel or the respiratory system. For example, a threshold trypsin concentration of 50 µg/ml (or an alternative threshold level) can be used to provide the requisite distinction between respiratory and small bowel placement after gastric placement has been excluded based upon the pepsin concentration. That is, a trypsin concentration of less than 50 µg/ml (or an alternative threshold level) will indicate that the feeding tube is positioned in respiratory system while a trypsin concentration greater than or equal to 50 µg/ml (or an alternative threshold level) will indicate that the feeding tube is positioned in the small bowel. Thus, a combination test employing pepsin and trypsin concentrations or threshold levels of pepsin and trypsin can be used to determine whether a feeding tube is positioned in the respiratory system, the stomach, or the small bowel.

As set forth herein, pepsin concentration and pH can be used to determine whether the feeding tube is positioned within the stomach. Thus, a combination test employing both pepsin concentration and pH will provide confirmation as to whether or not the feeding tube is positioned within the stomach. Such a combination test will preferably employ threshold levels such as those discussed herein. It will be appreciated that a combination test employing pepsin concentration and pH will not distinguish between respiratory and small bowel feeding tube placement.

From the foregoing discussion, it will be appreciated that the use of more than two of (a) bilirubin concentration; (b) pepsin concentration; (c) trypsin concentration; and (d) pH of the aspirated fluid may increase the accuracy of the determination of feeding tube location in some patients. For example, a method that considers bilirubin, pepsin, and trypsin concentrations may provide more accurate results than a method that considers only pepsin and trypsin. Method employing more than two of (a) bilirubin concentration; (b) pepsin concentration; (c) trypsin concentration; and (d) pH therefore are within the intended spirit and scope of the present invention.

Mathematical Model

The methods of the present invention can employ mathematical algorithms in order to facilitate a determination of feeding tube location. Two mathematical approaches are contemplated by the inventor. The first approach utilizes actual concentration values and pH values as determined in accordance with the methods of the present invention. The second approach utilizes dichotomized values for bilirubin, pepsin, and/or trypsin concentrations and pH. The inventor has determined that the dichotomized approach is the preferred approach in the context of the present invention. Utilization of absolute values for pH, pepsin, and trypsin is problematic in patients exhibiting abnormally high or low levels of one or more of pH, pepsin concentration, and trypsin concentration.

The use of dichotomized values is well known in the art of statistical analysis. A dichotomized value is a "1" or a "0" assigned to represent the concentration or pH determined in accordance with the methods of the present invention. For example, a pH above 5 (or some other threshold value) will be assigned a dichotomized value of "1" while a pH less than or equal to 5 will be assigned a dichotomized value of "0". In the case of trypsin, a concentration greater than 30 µg/ml (or some other threshold value) will be a assigned a dichotomized value of "1" while trypsin concentrations less than or equal to 30 µg/ml will be assigned a dichotomized value of "0". In the case of pepsin, a concentration greater than or equal to 100 µg/ml will be assigned a value of "1" while pepsin concentrations less than 100 µg/ml will be assigned a value of "0".

In one embodiment of the method of the present invention, a mathematical algorithm using pH, trypsin concentration, and pepsin concentration is used. In this embodiment, the following equation is used:

$$\text{Probability of Lung Placement} = \frac{1}{1 + e^{-z}}$$

z=(−9.9643)+(11.0697) (dichotomized pH)+(−14.0629) (dichotomized trypsin)+(−11.4144)(dichotomized pepsin)

e=base of natural logarithm (approximately 2.718)

The weights attributed to each of the dichotomized values in the above-referenced equation were determined using a software package, "Statistical Package for the Social Sciences", Version 6.1 ("SPSS"). Raw data collected by the inventor was analyzed using the "SPSS" software to produce these weights for the dichotomized values. It will be appreciated that modifications to these weights for the dichotomized values can be made without departing from the intended scope of the present as defined in the appended claims.

In the event that the probability of lung placement (as determined utilizing the above-referenced equation) is high, the health care professional preferably will take action to avoid the improper delivery of fluid into the lungs. Appropriate actions may include (a) removal of the feeding tube from the lung followed by placement of a feeding tube in the patient's gastrointestinal tract; and (b) undertaking an X-ray analysis of the patient to confirm feeding tube position.

In the event that the probability of lung placement (as determined utilizing the above-referenced equation) is low, the health care professional can proceed to determine whether the feeding tube is positioned in the stomach or in the small bowel. In this embodiment of the method of the present invention, such a determination is made using the following equation:

$$\text{Probability of Stomach Placement} = \frac{1}{1 + e^{-z}}$$

z=(2.2165)+(−1.6252)(dichotomized pH)+(−3.2687) (dichotomized trypsin)+(1.8560)(dichotomized pepsin)

e=base of natural logarithm (approximately 2.718)

The weights attributed to each of the dichotomized values in the above-referenced equation also were determined using raw data collected by the inventor and the "SPSS" software package. It will be appreciated that modifications to these weights for the dichotomized values can be made without departing from the intended scope of the present as defined in the appended claims.

The mathematical calculations discussed herein can be performed manually by a health care professional, but preferably are performed by a pre-programmed processing unit such as a computer or a hand-held calculator. Due to the portability and relatively low cost of programmable, hand-held calculators, the preferred method of the present invention utilizes a hand-held calculator. The calculator preferably is programmed such that it accepts raw data regarding pepsin concentration, trypsin concentration, and pH. The program in the calculator then calculates the dichotomized pH, the dichotomized pepsin, and the dichotomized trypsin values as well as performing the final mathematical calculations in accordance with the above-discussed formulae.

It will be readily apparent from the foregoing detailed description of the invention and from the illustrations thereof that numerous variations and modifications may be effected without departing from the true spirit and scope of the novel concepts or principles of this invention.

What is claimed is:

1. A method for determining placement of a distal end of a medical device, said method comprising:

taking a sample of a bodily fluid from a distal end of an in vivo medical device;

identifying a concentration in said sample of bodily fluid of at least one substance selected from a group consisting of bilirubin, pepsin, and trypsin; and determining placement of a distal end of an in vivo medical device using said concentration of said substance in said sample of bodily fluid.

2. A method in accordance with claim 1, wherein said method further comprises identifying a pH of said sample of bodily fluid, and wherein said determining placement step uses said pH of said sample of bodily fluid.

3. A method in accordance with claim 1, wherein said substance is bilirubin.

4. A method in accordance with claim 2, wherein said method further comprises identifying a pH of said sample of bodily fluid, and wherein said determining placement step uses said pH of said sample of bodily fluid.

5. A method in accordance with claim 2, wherein said method further comprises identifying a pepsin concentration of said sample of bodily fluid, and wherein said determining placement step uses said pepsin concentration of said sample of bodily fluid.

6. A method in accordance with claim 1, wherein said substance is pepsin.

7. A method in accordance with claim 6, wherein said method further comprises identifying a trypsin concentration of said sample of bodily fluid, and wherein said determining placement step uses said trypsin concentration of said sample of bodily fluid.

8. A method in accordance with claim 1, wherein said substance is trypsin.

9. A method in accordance with claim 8, wherein said method further comprises identifying a pH of said sample of bodily fluid, and wherein said determining placement step uses said pH of said sample of bodily fluid.

10. A method for determining placement of an in vivo medical device, said method comprising:

aspirating a sample of a bodily fluid from a distal end of an in vivo medical device;

identifying a concentration in said sample of bodily fluid of at least one substance selected from a group consisting of: pepsin, trypsin, and bilirubin; and determining placement of an in vivo medical device using said concentration of said at least one substance in said sample of bodily fluid.

11. A method in accordance with claim 10, wherein said method further comprises identifying a pH of said bodily fluid, and wherein said determining placement step uses said pH of said bodily fluid.

12. A method in accordance with claim 10, wherein said identifying step identifies more than one substance from said group consisting of: pepsin, trypsin, and bilirubin; and wherein said determining placement step utilizes concentrations of more than one substance selected from said group consisting of: pepsin, trypsin, and bilirubin.

* * * * *

UNITED STATES PATENT AND TRADEMARK OFFICE
CERTIFICATE OF CORRECTION

PATENT NO. : 5,891,054
DATED : April 6, 1999
INVENTOR(S) : Metheny et al.

It is certified that error appears in the above-identified patent and that said Letters Patent is hereby corrected as shown below:

Title page,

Please correct Title of Invention to read:

METHOD FOR DETERMINING FEEDING TUBE LOCATION

Signed and Sealed this

Tenth Day of April, 2001

*Attest:*

NICHOLAS P. GODICI

*Attesting Officer*   Acting Director of the United States Patent and Trademark Office